US009600991B2

(12) United States Patent
Chen et al.

(10) Patent No.: US 9,600,991 B2
(45) Date of Patent: Mar. 21, 2017

(54) SYSTEM AND METHOD FOR MEASURING PHYSIOLOGICAL PARAMETERS

(71) Applicant: BIONIME CORPORATION, Taichung (TW)

(72) Inventors: Chieh-Hsing Chen, Taichung (TW); Mao-Yi Chen, Taichung (TW); Ting-Yu Liu, Nantou County (TW); Chih-Lung Yeh, Taichung (TW)

(73) Assignee: BIONIME CORPORATION, Taichung (TW)

( * ) Notice: Subject to any disclaimer, the term of this patent is extended or adjusted under 35 U.S.C. 154(b) by 49 days.

(21) Appl. No.: 14/593,062

(22) Filed: Jan. 9, 2015

(65) Prior Publication Data

US 2015/0279186 A1   Oct. 1, 2015

(30) Foreign Application Priority Data

Mar. 31, 2014   (TW) .............................. 103112024 A

(51) Int. Cl.
| | |
|---|---|
| *H04B 5/00* | (2006.01) |
| *G08B 21/02* | (2006.01) |
| *A61B 5/15* | (2006.01) |
| *G08B 5/36* | (2006.01) |
| *A61B 5/145* | (2006.01) |

(52) U.S. Cl.
CPC ........ *G08B 21/02* (2013.01); *A61B 5/150358* (2013.01); *G08B 5/36* (2013.01); *H04B 5/0031* (2013.01); *H04B 5/0043* (2013.01); *H04B 5/0056* (2013.01); *A61B 5/14532* (2013.01); *A61B 5/14535* (2013.01); *A61B 5/14539* (2013.01); *A61B 2562/08* (2013.01); *A61B 2562/085* (2013.01); *H04B 5/0025* (2013.01); *H04B 5/0037* (2013.01); *H04B 5/0062* (2013.01)

(58) Field of Classification Search
CPC .................................................. A61B 5/15058
USPC ....................................................... 340/539.3
See application file for complete search history.

(56) References Cited

U.S. PATENT DOCUMENTS

| | | | |
|---|---|---|---|
| 2007/0270672 A1* | 11/2007 | Hayter | A61B 5/157 600/309 |
| 2009/0218891 A1* | 9/2009 | McCollough, Jr. | H02J 17/00 307/154 |
| 2012/0197090 A1* | 8/2012 | Chen | A61B 5/14532 600/301 |
| 2014/0021799 A1* | 1/2014 | Sankararamalingam | H04B 5/0037 307/104 |

(Continued)

*Primary Examiner* — Wayne Young
*Assistant Examiner* — Benyam Haile
(74) *Attorney, Agent, or Firm* — Volpe and Koenig, P.C.

(57) ABSTRACT

A method for measuring a physiological parameter is disclosed. The method includes providing an electronic device having a radio reader transmitting and receiving a radio signal; providing a physiological parameter measurement device configured with an energy storage module, a transmission module and a strip port for receiving a strip; energy storage in the physiological parameter measurement device in response to a radio energy storage signal transmitted from the electronic device until it reaches a sufficient energy status; and applying a sensing voltage to the strip via the strip port, receiving a sensing signal from the strip, and converting the sensing signal into a physiological parameter measurement signal by the physiological parameter measurement device under the sufficient energy status.

16 Claims, 5 Drawing Sheets

(56) References Cited

U.S. PATENT DOCUMENTS

2015/0288421 A1* 10/2015 Nambord .............. G06F 1/1632
455/41.1

* cited by examiner

SYSTEM AND METHOD FOR MEASURING PHYSIOLOGICAL PARAMETERS

CROSS-REFERENCE TO RELATED APPLICATION AND CLAIM OF PRIORITY

This application claims the benefit of Taiwan Patent Application No. 103112024, filed on Mar. 31, 2014, at the Taiwan Intellectual Property Office, the disclosures of which are incorporated herein in their entirety by reference.

FIELD OF THE INVENTION

The present invention relates to a measurement device, and more particularly to a system and method for measuring physiological parameters.

BACKGROUND OF THE INVENTION

In the developed network communication age, portable electronic devices, such as smart phones, tablets, notebooks, and even desktop computers configured with a radio communication interface card can provide many convenient services after cooperation with specific application programs. For example, transmitting and analyzing statistics of health care data, users can use designed application programs via the network transmission of the electronic devices, such as Short Distance/Near Field wireless Communication, Bluetooth, Wi-Fi etc. to transmit the physiological parameter measurement data collected from the physiological parameter measurement device to the smart phone. The daily measuring of physiological parameters, such as blood sugar concentration, cholesterol concentration, ureic acid concentration or pH value, and the variations thereof can be recorded and monitored. If there is an unusual condition in the measured physiological parameters, an alarm signal or medical treatment can be provided on time.

Although such a physiological parameter measurement device that cooperates with the application program of the electronic device can utilize the memory and operational functions of the electronic device adequately to simplify the components of a physiological parameter measurement device, the device still has a power supply component, such as a battery. This restriction adds to the volume of the device and the cost. A simple hardware structure and a physiological parameter measurement device with high common use, which can reduce cost, minimize the size of the device and reduce the weight, are urgently needed. The physiological parameter measurement and the transmission of the measurement data between the electronic device and the physiological parameter measurement device can enhance the convenience of use.

In order to overcome the drawbacks in the prior art, a system and a method for measuring physiological parameters are disclosed. The particular design in the present invention not only solves the problems described above, but is also easy to implement. Thus, the present invention has utility for industry.

SUMMARY OF THE INVENTION

In accordance with one aspect of the present invention, a method for measuring a physiological parameter is disclosed. The method includes steps of providing an electronic device having a radio reader transmitting and receiving a radio signal; providing a physiological parameter measurement device configured with an energy storage module, a transmission module and a strip port for receiving a test strip; storing energy in the physiological parameter measurement device in response to a radio energy storage signal transmitted from the electronic device until it reaches a sufficient energy status; and applying a sensing voltage to the strip, receiving a sensing signal from the strip, and converting the sensing signal into a physiological parameter measurement signal by the physiological parameter measurement device under the sufficient energy status.

In accordance with another aspect of the present invention, a system for measuring a physiological parameter is disclosed. The system includes an electronic device having an application program and a Near Field Communication (NFC) reader, wherein the NFC reader transmits an NFC scanning signal under operation of the application program. A physiological parameter measurement device having a Near Field Communication (NFC) tag and a physiological parameter measurement module, wherein the NFC tag transmits a response signal in response to the NFC scanning signal, and the NFC reader transmits an NFC energy storage signal to the energy storage module to store energy and cause the physiological parameter measurement device to enter a work status mode.

In accordance with a further aspect of the present invention, a physiological parameter measurement device which cooperates with an electronic device is disclosed. The electronic device has an application program and a radio reader transmitting and receiving a radio signal. The physiological parameter measurement device includes an energy storage module causing the electronic device to store energy in the physiological parameter measurement device in response to a radio energy storage signal transmitted from the electronic device until it reaches a sufficient energy status; and a transmission module coupled with the energy storage module, wherein the transmission module transmits a physiological parameter measurement signal in response to an instruction measurement signal from the electronic device and a sensing signal from a strip.

The objects and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Besides Bluetooth communication, new types of potable electronic devices also provide the function of Near Field Communication (NFC), which are usually configured with an NFC reader transmitting and receiving NFC signals. According to ISO18092/13157 regarding the standards of NFC, the setup time is less than 0.1 second, which is far faster than the setup time required by standard Bluetooth communication. In addition, the NFC signal can provide the function of storing energy. If an appropriate system and operation mode can be developed, NFC communication can be utilized to provide the physiological parameter measurement device with the functions of signal transmission and energy storage at the same time.

Both Bluetooth communication and Near Field Communication, as long as the electronic devices have a reader transmitting and receiving radio waves (bi-directional communication), are suitable for the system of the present invention to measure physiological parameters. For the purpose of convenience, the following embodiments disclose an example using NFC. A person ordinarily skilled in the art can realize that the present invention is suitable for other different types of radio communication.

Figure 1:
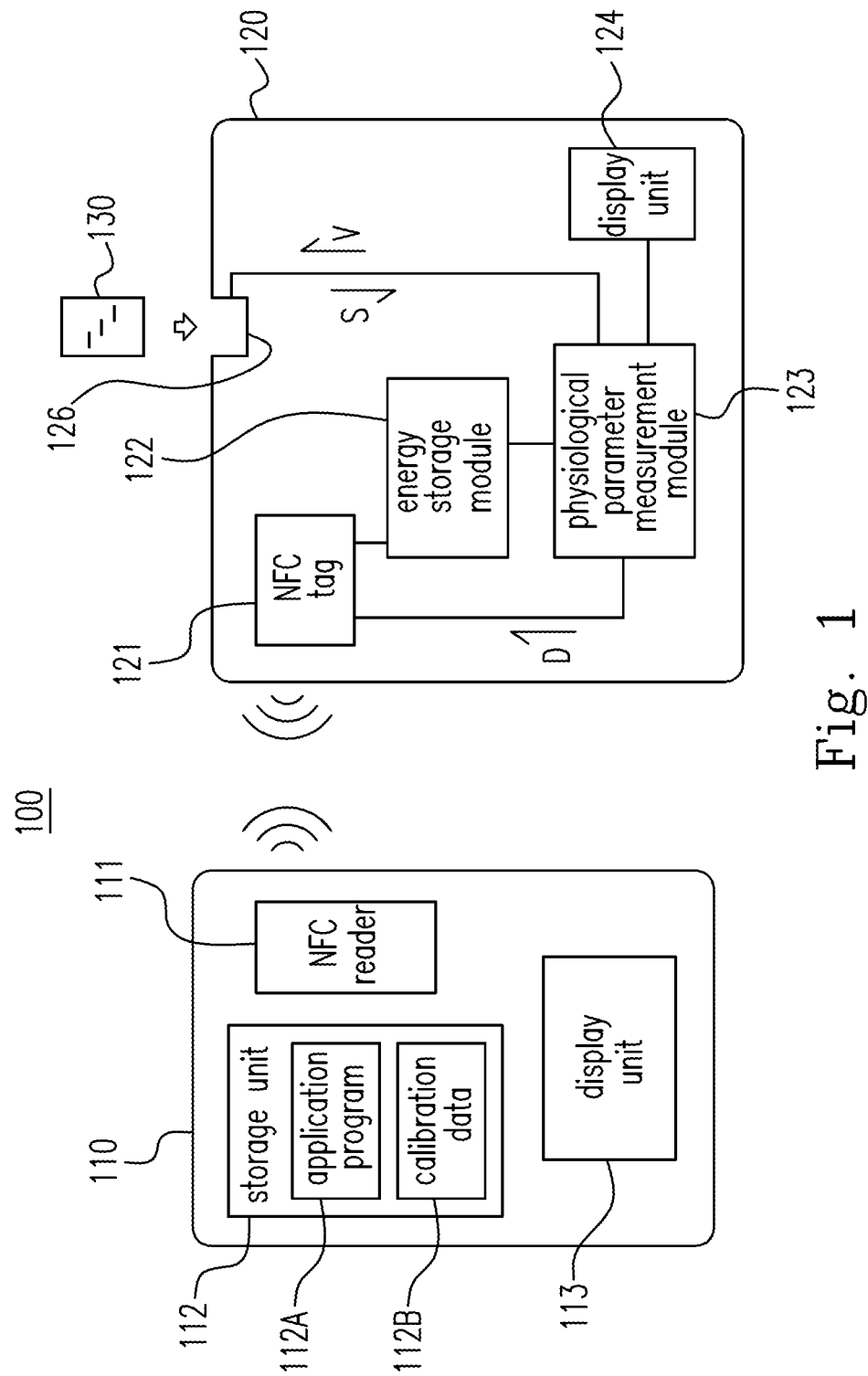
FIG. 1 shows a system for measuring physiological parameter according to a preferred embodiment of the present invention.

FIG. 1 is a diagram which shows a system for measuring physiological parameters, such as blood sugar concentration, cholesterol concentration, ureic acid concentration or pH value, according to a preferred embodiment of the present invention. As FIG. 1 shows, a system 100 includes an electronic device 110 and a physiological parameter measurement device 120. Under the work status of sufficient energy storage, the physiological parameter measurement device 120 can read a strip 130 to acquire the required physiological parameter measurement data. The electronic device is usually a portable electronic device, such as a mobile phone, tablet, notebook etc., and even a desktop computer configured with a radio communication interface card. The electronic device 110 has an NFC reader 111, storage unit 112 and display unit 113. Another electronic device having a built-in or external NFC reader is not limited herein. The NFC reader 111 can transmit and receive NFC signals. The display unit 113 can be a liquid crystal display, which can provide detailed frames and real-time information. The storage unit 112 is loaded with an application program 112A. Because the characteristics of the physiological parameter measurement strips from different batches have quite large variations, according to a preferred embodiment, the storage unit 112 is loaded with calibration data 112B corresponding to the strip 130, which can be provided to the application program 112A to calibrate the measured data.

The physiological parameter measurement device 120 is configured with an NFC tag 121, energy storage module 122, physiological parameter measurement module 123, display unit 124 and strip port 126. As FIG. 1 shown, the NFC tag 121, energy storage module 122 and physiological parameter measurement module 123 are coupled with each other, and the physiological parameter measurement module 123 is coupled with the display unit 124 and the strip port 126. The NFC tag 121 in the physiological parameter measurement device 120 and the NFC reader 111 in the electronic device 110 can transmit various NFC signals, such as an NFC scanning signal, response signal, NFC energy storage signal, finishing energy storage signal, physiological parameter measurement signal etc. to each other via NFC. After system 100 has reached sufficient energy storage and under a work status mode, the strip 130 with the sample is configured in the strip port 126. The physiological parameter measurement module 123 can apply sensing voltage to the strip 130 to cause the strip 130 to generate a sensing signal in response to the voltage. The sensing signal from the strip 130 is converted to a physiological parameter measurement signal, and the NFC tag 121 is instructed to transmit the physiological parameter measurement signal to the electronic device 110 via NFC. Finally, the physiological parameter measurement signal is calculated and calibrated by the application program to obtain an accurate physiological parameter value. The display unit 124 is configured to display the energy storage status of the physiological parameter measurement device 120, the connection status of the NFC signal, a different operation status or physiological parameter value, and the display unit 124 can be a screen, indication lamp or speaker.

There are usually measurement variations resulting from the production process or materials among different batches of the strip 130 for physiological parameter measurement. The calibration data for an individual strip can be obtained during the production test stage to calibrate the measured data more accurately. In another embodiment, the storage unit 112 is loaded with calibration data 112B corresponding to the strip 130, which can be transmitted to the physiological parameter measurement device 120 via the radio communication between the electronic device 110 and the physiological parameter measurement device 120. After the physiological parameter measurement module 123 obtains the calibrated physiological parameter value, the calibrated physiological parameter value is displayed on the display unit 113 of the electronic device or the display unit 124 of the physiological parameter measurement device 120.

As the operation steps proceed, the application program on the display unit 113 of the electronic device 110 can be used to display the screens of the system 100 under different status modes, and provide the user with an indication of operation or display the value. FIGS. 2A-2D show the embodiments of the screens of the display unit 113 under different status modes. In another embodiment, if the physiological parameter measurement device 120 has the display unit 124, the display unit 124 can cooperate with the electronic device 110 to show the screens under different status, such as energy storage status, connection status of the NFC signal, different operation status or physiological parameter value. A person ordinarily skilled in the art can design any application according to necessity.

Figure 2B:
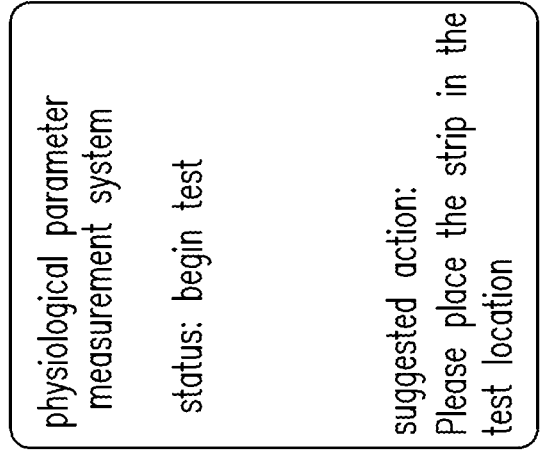
FIG. 2B shows the frame of the display unit of the electronic device under the condition that the physiological parameter measurement device has been started.
Figure 2A:
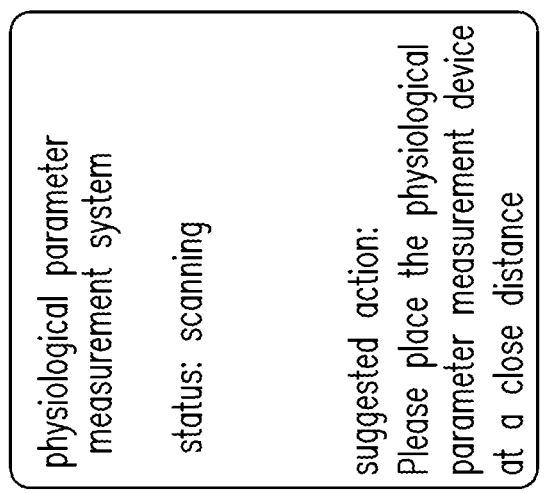
FIG. 2A shows the frame of the display unit of the electronic device under the condition of scanning an beginning the test.
Figure 3:
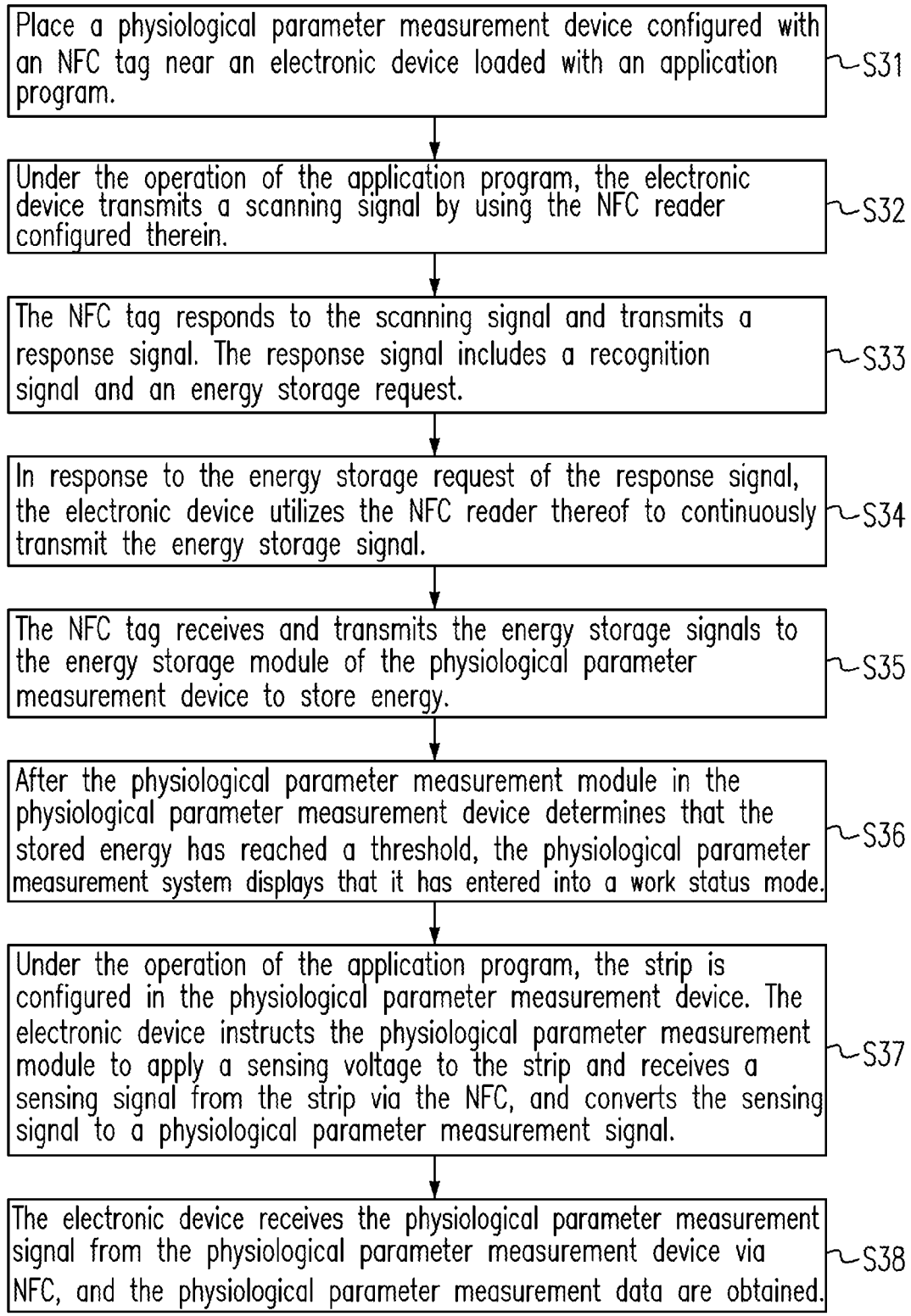
FIG. 3 is a simplified flow chart which shows the processes of the physiological parameter measurement system and method according to the present invention.

Please refer to FIG. 3, which is a flow chart of the physiological parameter measurement system and method according to the present invention. First, place the physiological parameter measurement device 120 configured with the NFC tag 121 near or contact the electronic device 110 loaded with the application program 112A (step S31), herein physiological parameter measurement device 120 could integrate with a case of electronic device 110. Once the application program 112A suitable for the present invention is started on the electronic device 110, under the operation of the application program 112A, the electronic device 110 transmits a scanning signal by using the NFC reader 111 configured therein (step S32). In this process, the display unit 113 shows the screen as shown in FIG. 2A. According to the general standards for NFC, the effective distance for NFC is within 100 cm, preferably within 20 cm. Therefore, the instruction on the screen in FIG. 2A is used to remind the user to place the physiological parameter measurement device 120 near the electronic device 110. The physiological parameter measurement device 120 in the present invention does not need a power source, because the energy is stored via the electronic device 110, and has sufficient energy to enter a work status mode. The NFC tag 121 inside the physiological parameter measurement device 120 has a radio chip and an antenna, and the NFC tag 121 and the NFC reader will initiate electromagnetic induction to convert the electromagnetic radiation into electric energy via a coil. The electric energy is provided to the radio chip's operation and to make the radio chip to transmit electromagnetic radiation responding to the NFC reader to respond the scanning signal and transmit a response signal in real time. The response signal includes a recognition signal and a storing energy request (step S33), and the electric energy is transmitted to the storing module to store energy in, for example, a capacitor.

A person ordinarily skilled in the art can realize that NFC is usually a one-to-one match where the devices are near each other but no need to touch. After the electronic device 110 receives the response signal, the physiological parameter measurement device 120 can be identified from the recognition signal therein to complete the match between the devices. In response to the energy storage request, the electronic device 110 utilizes the NFC reader 111 to continuously transmit the energy storage signal (step S34). To ensure that the physiological parameter measurement device 120 has enough electric energy to maintain the work status mode, the NFC reader 111 transmits the energy storage signal continuously to cause the electronic device 110 to provide electric energy to the physiological parameter measurement device 120. According to an embodiment of the present invention, the transmission time of the NFC energy storage signal can be distinct from that of the other NFC signal to avoid the NFC energy storage signal interfering with the other NFC signal. The method for separating the signal transmission time can set the time period of the transmission of the NFC energy storage signal in a specific time period, for example, the third time period of every five time periods, and the transmission of the other NFC signal would then avoid the third time period.

After the NFC tag 121 receives the energy storage signals, the energy storage signals are transmitted to the energy storage module 122 of the physiological parameter measurement device 120 to store energy (step S35). According to an embodiment, energy storage module 122 references a voltage value and compares the voltage value with the one accumulated in an electrical charge storage component (not shown). When the voltage value accumulated in the electrical charge storage component reaches a threshold, the stored electric power at least reaches a threshold to cause the electric charge storage component to supply a sensing voltage to begin the physiological parameter measurement. A person ordinarily skilled in the art can realize that the voltage threshold is at least 0.7 V. In another embodiment, the electric charge storage component can cooperate with a voltage-doubling rectifier. The voltage threshold can be set to at least 0.3 V depending on the specifications of the electronic components to be configured, and the other voltage value is also possible. In addition, the threshold may be the amount of electrical charge, time of energy storage, etc. to ensure that there is no shortage of electric power for the physiological parameter measurement device 120 under the work status mode. After the physiological parameter measurement module 123 in the physiological parameter measurement device 120 determines that the stored energy has reached a threshold, the NFC tag 121 transmits a finishing energy storage signal to cause the physiological parameter measurement system 100 to display that it is in a work status mode (step S36). The display unit 113 of the electronic device 110 can display the screen as shown in FIG. 2B, or the physiological parameter measurement module 123 can instruct the display unit 124 of the physiological parameter measurement device 120 to activate a light, voice or screen image signal, indicating that the physiological parameter measurement device 120 has completed the energy storage and is able to enter a work status mode. The stored energy is enough to begin at least one physiological parameter measurement. In another embodiment, the physiological parameter measurement device 120 does not include an energy storage module. When NFC tag 121 receives the energy storage signal, the electric power can be directly transmitted to the physiological parameter measurement module 123 to begin the analyte measurement.

Figure 2D:
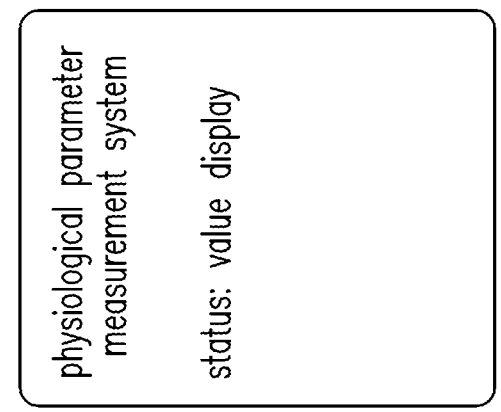
FIG. 2D shows the frame of the display unit of the electronic device under the status of displaying a value in the system.
Figure 2C:
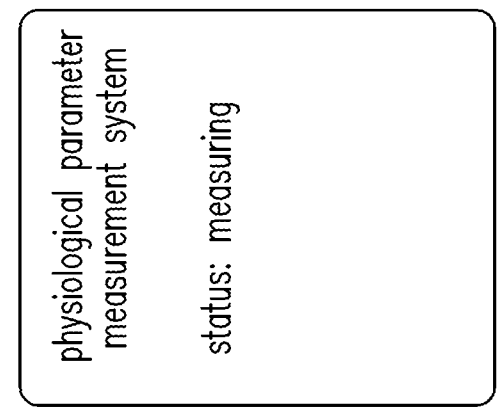
FIG. 2C shows the frame of the display unit of the electronic device in the work status mode of the system.

When the system 100 is in the work status mode, the strip 130 can be configured in the physiological parameter measurement device 120 under the operation of the application program 112A. The electronic device 110 instructs the physiological parameter measurement module 123 to apply a sensing voltage V to the strip 130 and receive a sensing signal S from the strip 130, and converts the sensing signal S to a physiological parameter measurement signal D (step S37). The display unit 113 displays the screen shown in FIG. 2C. The strip 130 can be inserted into the strip port 126, and then the sample, such as blood or bodily fluid, is applied to the strip 130, or the sample is applied to the strip 130 first, and then the strip 130 is inserted into the strip port 126. The electronic device 110 receives the physiological parameter measurement signal from the physiological parameter measurement device 120 via NFC, and the physiological parameter measurement data is obtained after the operation (step S38), or the physiological parameter measurement signal is directly calculated in the physiological parameter measurement device 120, and the physiological parameter value is shown on the screen of the physiological parameter measurement device 120. In another embodiment, when the system 100 is in a work status mode, the strip 130 can be configured in the physiological parameter measurement device 120 and be measured directly without an instruction via NFC. After the physiological parameter measurement module 123 senses the insertion of the strip 130, physiological parameter measurement module 123 applies the sensing voltage V to the strip 130 and receives the sensing signal S from the strip 130, and converts the sensing signal S to a physiological parameter measurement signal D. The physiological parameter measurement data can be displayed on the display unit 113, and the display unit 113 displays a screen as shown in FIG. 2D.

Figure 4:
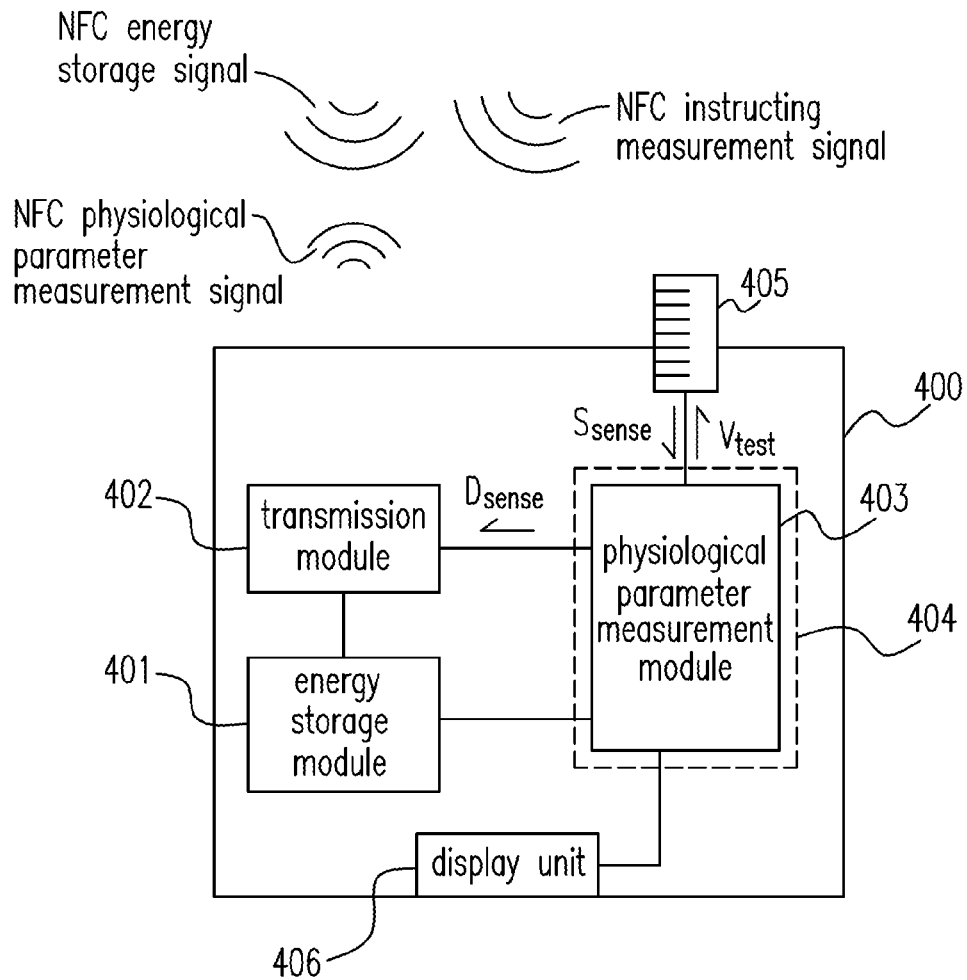
FIG. 4 shows the physiological parameter measurement device according to another preferred embodiment of the present invention.

Please refer to FIG. 4, which shows the physiological parameter measurement device 120 for measuring the physiological parameters according to another preferred embodiment of the present invention. A physiological parameter measurement device 400 includes an energy storage module 401, transmission module 402, physiological parameter measurement module 403 and shield device 404, and can be configured with the strip 405 with a sample thereon. As shown in FIG. 4, the energy storage module 401, the transmission module 402 and the physiological parameter measurement module 403 are coupled with each other, the physiological parameter measurement module 403 is coupled with a strip 405, and the shield device 404 is configured on at least one side of the physiological parameter measurement module 403 to block NFC signals to allow the transmission module to continuously receive the energy storage signal, and the physiological parameter measurement module 403 begins the physiological parameter signal measurement without disturbance. The physiological parameter measurement device 400 cooperates with an electronic device (not shown) loaded with an application program. The energy storage module 401 causes the electronic device to store energy in the physiological parameter measurement device 400 in response to an NFC energy storage signal from the electronic device until it reaches a sufficient energy status. When the energy status is sufficient, the physiological parameter measurement device 400 receives an NFC measurement signal from the electronic device, the physiological parameter measurement module 403 transmits a test voltage $V_{test}$ to the strip 405, receives an analog sensing signal $S_{sense}$, and converts the sensing signal $S_{sense}$ to a digital sensing signal $D_{sense}$. The transmission module 402 transmits an NFC physiological parameter measurement signal according to the digital sensing signal $D_{sense}$ to cause the electronic device to begin the subsequent signal read and display. Furthermore, the read value can be edited and operated via the function of data analysis provided by the application program. The configuration and the operation method of the electronic device are the same as those in the previous embodiments, and are not described again here.

When the physiological parameter measurement module 403 ascertains the sufficient energy status, the physiological parameter measurement module 403 instructs the transmission module 402 to transmit a finishing energy storage signal. The condition of ascertaining the sufficient energy status can be that a stored voltage in the energy storage module exceeds a threshold. The previous description has introduced the setting of the threshold and there is no need to describe it again here.

If the physiological parameter measurement and reception of the energy storage signal happen at the same time, the energy storage signal could easily disturb the physiological parameter measurement module 403. To avoid any interference from the NFC energy storage signal to the physiological parameter measurement module 403, in addition to the method of configuring the shield device 404, the transmission time of the NFC energy storage signal and the other NFC signals can be separated. As a result, the NFC energy storage signal can avoid interfering with the other NFC signals, or a module for detecting and calibrating the interference signals may be installed.

In another embodiment, the physiological parameter measurement device 400 can include a display unit 406. There are usually measuring variations resulting from the production process or materials among different batches of the strip 405 for physiological parameter measurements. The calibration data for each individual strip can be obtained during the production test stage to calibrate the measurement data more accurately. In another embodiment, the calibration data on the electronic device (not shown) can be transmitted to the physiological parameter measurement module 403 via radio communication, the physiological parameter measurement module 403 utilizes the calibration data to calibrate the physiological parameter value, and then the calibrated value is shown on the electronic device or the display unit 406 of the physiological parameter measurement device 400.

In addition, with the rising development of wireless charging technology, the main alliances include Wireless Power Consortium (WPC), Alliance for Wireless Power (A4WP) and Power Matters Alliance (PMA). The wireless charging technology is achieved by magnetic induction or magnetic resonance, and WPC's Qi wireless charging specification is the most widely known. A Qi receiver has characteristics of being simple to make, miniature and low-priced. Therefore the tag 121 of the physiological parameter measurement device 120 in the present invention can be a WPC Qi receiver or a wireless charging receiver from A4WP or PMA. Any receiver with the wireless charging function is suitable for use in the physiological parameter measurement system disclosed in the present invention. It is worth mentioning that after the present system achieves the signal exchange and match via NFC, the device can be minimized, and the signal exchange and efficacy of energy storage are highly increased via the wireless charging technology.

The system and method disclosed in the present invention allows the physiological parameter measurement device to be free from a power source, which is environmentally friendly and reduces the cost of energy. The physiological parameter measurement device can store energy and perform physiological parameter measurements wirelessly. The cost for manufacturing the physiological parameter measurement device is reduced, the device can be small and light weight, and convenient and effective operation is provided to the user.

Embodiments

1. A method for measuring a physiological parameter, comprising steps of providing an electronic device having a radio reader transmitting and receiving a radio signal; providing a physiological parameter measurement device configured with an energy storage module, a transmission module and a strip port for receiving a strip; energy storage in the physiological parameter measurement device in response to a radio energy storage signal transmitted from the electronic device until it reaches a sufficient energy status; and applying a sensing voltage to the strip via the strip port, receiving a sensing signal from the strip, and converting the sensing signal into a physiological parameter measurement signal by the physiological parameter measurement device under the sufficient energy status.

2. The method of Embodiment 1, wherein the radio reader transmits a scanning signal to the physiological parameter measurement device, and the transmission module transmits a response signal in response to the scanning signal.

3. The method of Embodiments 1-2, wherein the response signal includes a recognition signal and an energy storage request.

4. The method of Embodiments 1-3, wherein the physiological parameter measurement device references to a threshold to determine whether to transmit a finishing energy storage signal or not.

5. The method of Embodiments 1-4, wherein the threshold includes a voltage value.

6. The method of Embodiments 1-5, further comprising steps of, in response to receipt of the finishing energy storage signal from the transmission module by the radio reader, causing at least one of the electronic device and the physiological parameter measurement device to display a work status mode of the physiological parameter measurement device according to the finishing energy storage signal.

7. The method of Embodiments 1-6, further comprising a step of measuring the physiological parameter by the physiological parameter measurement device in response to a measurement signal transmitted from the electronic device.

8. The method of Embodiments 1-7, wherein the electronic device is configured with a storage unit having an application program and calibration data corresponding to the strip, and the electronic device and the physiological parameter measurement device are each configured with a display unit.

9. The method of Embodiments 1-8, further comprising steps of obtaining the calibration data by the physiological parameter measurement device via a radio communication between the transmission module and the radio reader, calibrating the physiological parameter measurement signal based on the calibration data to obtain a calibrated physiological parameter value, and displaying the calibrated physiological parameter value on the display unit of the physiological parameter measurement device.

10. The method of Embodiments 1-9, further comprising a step of transmitting the physiological parameter measurement signal to the electronic device by the physiological parameter measurement device via a radio communication between the transmission module and the radio reader, calibrating the physiological parameter measurement signal by the application program according to the calibration data to obtain a calibrated physiological parameter value, and displaying the calibrated physiological parameter value on the display unit of the electronic device.

11. The method of Embodiments 1-10, further comprising steps of measuring the physiological parameter by the physiological parameter measurement device in response to an instructing measurement signal transmitted from the electronic device after the strip is configured in the strip port.

12. The method of Embodiments 1-11, wherein the transmission module is a Near Field Communication tag, and the radio reader is a Near Field Communication reader.

13. A system for measuring a physiological parameter, comprising an electronic device having an application program and a Near Field Communication (NFC) reader, wherein the NFC reader transmits an NFC scanning signal under an operation of the application program; and a physiological parameter measurement device having a Near Field Communication (NFC) tag and a physiological parameter measurement module, wherein the NFC tag transmits a response signal in response to the NFC scanning signal, and transmits an NFC energy storage signal from the NFC reader to the physiological parameter measurement module to cause the physiological parameter measurement module to enter into a work status mode.

14. The system of Embodiment 13, wherein the physiological parameter measurement device is further configured with an energy storage module and a strip port for receiving a strip, and in the work status mode, when the strip port receives the strip with a sample, the physiological parameter measurement module applies a sensing voltage to the strip and receives a sensing signal from the strip, and the sensing signal is converted into a physiological parameter measurement signal.

15. The system of Embodiment 13, wherein the physiological parameter measurement device references to a threshold to determine whether to transmit a finishing energy storage signal or not, and the threshold includes a voltage.

16. A physiological parameter measurement device which cooperates with an electronic device, wherein the electronic device has an application program and a radio reader transmitting and receiving a radio signal, the physiological parameter measurement device has an energy storage module causing the electronic device to store energy in the physiological parameter measurement device in response to a radio energy storage signal transmitted from the electronic device until it reaches a sufficient energy status; and a transmission module coupled with the energy storage module, wherein the transmission module transmits a physiological parameter measurement signal in response to a measurement signal from the electronic device and a sensing signal from a strip.

17. The device of Embodiment 16, further comprising a physiological parameter measurement module coupled with the energy storage module and the transmission module, wherein when a storage voltage in the energy storage module exceeds a threshold, the physiological parameter measurement module instructs the transmission module to transmit a finishing energy storage signal to the electronic device; and on the condition that the transmission module receives and conveys the instructing measurement signal from the electronic device, the physiological parameter measurement module instructs the transmission module to transmit the physiological parameter measurement signal according to the sensing signal.

18. The device of Embodiments 16-17, further comprising a shield device configured on at least one side of the physiological parameter measurement module to block a energy storage request signal transmitted from the transmission module.

19. The device of Embodiments 16-18, wherein the electronic device is configured with a storage unit having the application program and calibration data corresponding to the strip, and the electronic device and the physiological parameter measurement device are each configured with a display unit.

20. The device of Embodiments 16-19, wherein the physiological parameter measurement module transmits the physiological parameter measurement signal to the electronic device via a radio communication between the transmission module and the radio reader, the application program calibrates the physiological parameter measurement signal according to the calibration data to obtain a calibrated physiological parameter measurement value to be displayed on the display unit of the electronic device.

21. The device of Embodiments 16-20, wherein the calibration data corresponding to the strip is transmitted to the physiological parameter measurement module via a radio communication between the transmission module and the radio reader, the physiological parameter measurement module calibrates a physiological parameter measurement value based on the calibration data to obtain a calibrated value, and the calibrated value is displayed on the display unit of the physiological parameter measurement device.

Based on the above, the present invention effectively solves the problems and drawbacks in the prior art, and thus it meets the demands of industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:
1. A method for measuring a physiological parameter, comprising steps of:

providing an electronic device having a radio reader transmitting and receiving a radio signal;
providing a physiological parameter measurement device configured with an energy storage module, a transmission module and a strip port for receiving a strip;
energy storage in the physiological parameter measurement device in response to a radio energy storage signal transmitted from the electronic device until it reaches a sufficient energy status, wherein the physiological parameter measurement device references to a threshold to determine whether to transmit a finishing energy storage signal or not, and the threshold includes a voltage value;
in response to the receipt of the finishing energy storage signal from the transmission module by the radio reader, causing at least one of the electronic device and the physiological parameter measurement device to display a work status mode of the physiological parameter measurement device according to the finishing energy storage signal; and
applying a sensing voltage to the strip via the strip port, receiving a sensing signal from the strip, and converting the sensing signal into a physiological parameter measurement signal by the physiological parameter measurement device under the sufficient energy status.

2. The method as claimed in claim 1, wherein the radio reader transmits a scanning signal to the physiological parameter measurement device, and the transmission module transmits a response signal in response to the scanning signal.

3. The method as claimed in claim 2, wherein the response signal includes a recognition signal and an energy storage request.

4. The method as claimed in claim 1, further comprising a step of:
measuring the physiological parameter with the physiological parameter measurement device in response to an instruction measurement signal transmitted from the electronic device.

5. The method as claimed in claim 4, wherein the electronic device is configured with a storage unit having an application program and calibration data corresponding to the strip, and the electronic device and the physiological parameter measurement device are each configured with a display unit.

6. The method as claimed in claim 5, further comprising steps of:
obtaining the calibration data by the physiological parameter measurement device via a radio communication between the transmission module and the radio reader, calibrating the physiological parameter measurement signal based on the calibration data to obtain a calibrated physiological parameter value, and displaying the calibrated physiological parameter value on the display unit of the physiological parameter measurement device.

7. The method as claimed in claim 5, further comprising a step of:
transmitting the physiological parameter measurement signal to the electronic device by the physiological parameter measurement device via a radio communication between the transmission module and the radio reader, calibrating the physiological parameter measurement signal by the application program according to the calibration data to obtain a calibrated physiological parameter value, and displaying the calibrated physiological parameter value on the display unit of the electronic device.

8. The method as claimed in claim 1, further comprising steps of:
measuring the physiological parameter by the physiological parameter measurement device in response to an instruction measurement signal transmitted from the electronic device after the strip is configured in the strip port.

9. The method as claimed in claim 1, wherein the transmission module is a Near Field Communication tag, and the radio reader is a Near Field Communication reader.

10. A system for measuring a physiological parameter, comprising:
an electronic device having an application program and a Near Field Communication (NFC) reader, wherein the NFC reader transmits an NFC scanning signal under operation of the application program; and
a physiological parameter measurement device having a Near Field Communication (NFC) tag, a physiological parameter measurement module, a transmission module, a shield device, and a strip port for receiving a strip, wherein
the physiological parameter measurement module is coupled with the transmission module, and the system is configure such that the NFC tag transmits a response signal in response to the NFC scanning signal, and transmits an NFC energy storage signal from the NFC reader to the physiological parameter measurement module to cause the physiological parameter measurement module to enter a work status mode, the physiological parameter measurement device references to a threshold to determine whether to transmit a finishing energy storage signal or not, the threshold includes a voltage value, and in response to the receipt of the finishing energy storage signal by the NFC reader, at least one of the electronic device and the physiological parameter measurement device displays a work status mode of the physiological parameter measurement device according to the finishing energy storage signal, and
the shield device is configured on at least one side of the physiological parameter measurement module to block an energy storage signal transmitted from the transmission module, the physiological parameter measurement device is configured to apply a sensing voltage to a strip received in the strip port via the strip port and receive a sensing signal from the strip.

11. The system as claimed in claim 10, wherein the physiological parameter measurement device is further configured with an energy storage module, and under the work status mode, when the strip port receives the strip with a sample, the physiological parameter measurement module is configured to convert the sensing signal into a physiological parameter measurement signal.

12. A physiological parameter measurement device that cooperates with an electronic device, wherein the electronic device has an application program and a radio reader transmitting and receiving a radio signal, the physiological parameter measurement device comprising:
a strip port for receiving a strip;
an energy storage module configured to cause the electronic device to store energy in the physiological parameter measurement device in response to a radio energy storage signal transmitted from the electronic device until it reaches a sufficient energy status, the physiological parameter measurement device configure to reference to a threshold to determine whether to transmit a finishing energy storage signal or not, the threshold includes a voltage value, and in response to the receipt of the finishing energy storage signal by the radio reader, at least one of the electronic device and the physiological parameter measurement device configured to display a work status mode of the physiological parameter measurement device according to the finishing energy storage signal;

a transmission module coupled with the energy storage module, wherein the transmission module is configured to transmit a physiological parameter measurement signal in response to an instruction measurement signal from the electronic device and a sensing signal from a strip received in the strip port;

a physiological parameter measurement module coupled with the energy storage module and the transmission module, wherein the physiological parameter module is configured to apply a sensing voltage to the strip via the strip port and convert the sensing signal from the strip to the physiological parameter measurement signal; and a shield device configured on at least one side of the physiological parameter measurement module to block an energy storage request signal transmitted from the transmission module.

13. The device as claimed in claim 12, wherein:

when a storage voltage in the energy storage module exceeds a threshold, the physiological parameter measurement module instructs the transmission module to transmit a finishing energy storage signal to the electronic device; and on the condition that the transmission module receives and conveys the instructing measurement signal from the electronic device, the physiological parameter measurement module instructs the transmission module to transmit the physiological parameter measurement signal according to the sensing signal.

14. The device as claimed in claim 13, wherein the electronic device is configured with a storage unit having the application program and calibration data corresponding to the strip, and the electronic device and the physiological parameter measurement device are each configured with a display unit.

15. The device as claimed in claim 14, wherein the physiological parameter measurement module is configured to transmit the physiological parameter measurement signal to the electronic device via a radio communication between the transmission module and the radio reader, the application program is configured to calibrate the physiological parameter measurement signal according to the calibration data to obtain a calibrated physiological parameter measurement value to be displayed on the display unit of the electronic device.

16. The device as claimed in claim 14, configured such that the calibration data corresponding to the strip is transmitted to the physiological parameter measurement module via a radio communication between the transmission module and the radio reader, the physiological parameter measurement module calibrates a physiological parameter measurement value based on the calibration data to obtain a calibrated value, and the calibrated value is displayed on the display unit of the physiological parameter measurement device.

* * * * *